US012715185B2

(12) United States Patent
MacMullin et al.

(10) Patent No.: US 12,715,185 B2
(45) Date of Patent: Aug. 25, 2026

(54) PRESCRIPTION EYEWEAR WITH PHOTOPHOBIC RESPONSE CONTROL AND/OR CIRCADIAN CYCLE MODULATION CAPABILITIES

(71) Applicant: MATAP II LLC, Aventura, FL (US)

(72) Inventors: Thomas D. MacMullin, Boscawen, NH (US); Bonnie Simmons, Boscawen, NH (US)

(73) Assignee: MATAP II LLC, Aventura, FL (US)

( * ) Notice: Subject to any disclaimer, the term of this patent is extended or adjusted under 35 U.S.C. 154(b) by 677 days.

(21) Appl. No.: 18/160,657

(22) Filed: Jan. 27, 2023

(65) Prior Publication Data

US 2024/0252038 A1 Aug. 1, 2024

(51) Int. Cl.

*B29D 11/00* (2006.01)
*A61F 2/14* (2006.01)
*A61B 3/10* (2006.01)
*A61F 9/008* (2006.01)

(52) U.S. Cl.

CPC .......... *B29D 11/00009* (2013.01); *A61F 2/14* (2013.01); *A61B 3/10* (2013.01); *A61F 9/00812* (2013.01); *G02C 2202/16* (2013.01)

(58) Field of Classification Search

CPC .......... A61B 3/10; A61F 2/14; A61F 9/00812; A61F 9/022; A61F 2009/021; G02C 2202/16; G02C 7/10; G02C 7/104; B29D 11/00009; G02B 5/223

See application file for complete search history.

(56) References Cited

U.S. PATENT DOCUMENTS 5,271,872 A * 12/1993 Sallavanti .............. G02B 5/223 359/356
2002/0159155 A1* 10/2002 O'Brien ................... G02B 5/26 359/601
2003/0075816 A1* 4/2003 Buazza .................. G02B 1/041 249/105
2009/0268157 A1* 10/2009 Krieg-Kowald ....... G02B 5/223 351/159.63
2017/0075143 A1* 3/2017 Saylor .................... G02C 7/101
2018/0203171 A1* 7/2018 Mcpherson ............ G02C 7/104
2019/0151152 A1* 5/2019 Goebel Quintana .... G02C 7/10
2019/0196071 A1* 6/2019 Barrett .............. G02F 1/133514
2023/0204982 A1* 6/2023 Boyles .................. G02C 7/104 351/159.65

* cited by examiner

*Primary Examiner* — Matthew Y Lee
(74) *Attorney, Agent, or Firm* — Workman Nydegger

(57) ABSTRACT

A lens blank includes a first layer and a second layer. The first layer has an anterior surface and a posterior surface and is formed a base material and one or more energy absorptive dyes generally uniformly dispersed throughout the base material. The one or more dyes are configured to absorb electromagnetic energy. The second layer is bonded or permanently attached to the posterior surface of the first layer and is formed of a generally clear base material.

17 Claims, 3 Drawing Sheets

PRESCRIPTION EYEWEAR WITH PHOTOPHOBIC RESPONSE CONTROL AND/OR CIRCADIAN CYCLE MODULATION CAPABILITIES

BACKGROUND

1. Technical Field

The present application relates to eyewear. More specifically, the present application relates to eyewear with one or more lenses that can be polished with a user's prescription and that can reduce the frequency and/or severity of photophobic responses or modulate circadian cycles.

2. The Relevant Technology

The retina of the eye contains various photoreceptor cells. These photoreceptor cells include rods (which are involved in black-and-white and low light vision), cones (which are involved in daytime vision and color perception), and melanopsin ganglion cells. The melanopsin ganglion cells are photosensitive. This photosensitivity can transmit pain through the pain pathways of the brain. It has been demonstrated previously that modulating ambient light through the use of spectacle tints can be effective in the treatment of light-sensitive neurological conditions including migraine and benign essential blepharospasm.

In addition to pain pathways, melanopsin ganglion cells also connect to the suprachiasmatic nucleus, where they participate in entrainment of circadian rhythms. All animals have an intrinsic "clock" that synchronizes them with the earth's light/dark cycle of 24 hours. This clock establishes an internal rhythm of about ("circa") one day ("dian"). However, in order to stay optimally synchronized with the dark/light cycle, the body's internal clock must be reset each day. This entrainment occurs when light in the environment is absorbed by the melanopsin ganglion cells and a signal is transmitted to that part of the brain that serves as the body's "master clock," the suprachiasmatic nucleus.

Rhodopsin is the photosensitive molecule in the rods and cones of the eye. Rhodopsin has two metastable isomers including an active and an inactive state. When exposed to light, the rhodopsin isomerizes to an inactive isoform. The inactive isoform of rhodopsin can be recycled in the retinoid cycle. During the retinoid cycle, the rhodopsin leaves the photoreceptor and enters the retinal pigment epithelium. After being recycled to an active isoform, the rhodopsin returns to the photoreceptor. The melanopsin of the melanopsin ganglion cells is believed to undergo a similar process.

Various types of eyewear have been developed in efforts to mitigate some of the above-noted photophobic responses and/or to modulate circadian cycles. Despite these efforts, there are various areas where improvement can be made. For instance, typical eyewear that attempts to provide the noted benefits is not suitable for having a user's prescription polished therein. As a result, for a user that wears corrective/prescription lenses (e.g., eyeglasses), the user would have to wear two sets of eyewear—the normal vision correction eyeglasses and the light filtering eyewear—in order to see clearly and to realize the photophobic response reduction or circadian cycle modulation.

Some efforts have been made to provide prescription and light filtering eyewear. For instance, tinted mineral glass has been used to make lenses for such eyewear. While the mineral glass may be polished with a user's prescription, it presents other undesirable characteristics. For instance, when the prescription is polished into the glass, portions of the glass are thinned out more than other parts. This results in a gradation of colors across the glass (e.g., due to less tint in the thin or polished areas), which can be distracting to or impair the vision of the user and/or may negatively impact the optical characteristics of the eyewear. Furthermore, in order to be able to apply a range of different prescriptions, the mineral glass typically has to be relatively thick, which can lead to the undesirable Coke-bottle effect.

In light of the above, there remains room for improvement in the area of eyewear, particularly as it relates to eyewear that provides a corrective prescription and that controls photophobic responses or modulates circadian cycles.

BRIEF SUMMARY

The present application relates to eyewear. More specifically, the present application relates to eyewear with one or more lenses that can be polished with a user's prescription and that can reduce the frequency and/or severity of photophobic responses or modulate circadian cycles.

For instance, in one embodiment, a lens blank may include a first layer and a second layer. The first layer may have an anterior surface and a posterior surface and be formed a base material and one or more energy absorptive dyes generally uniformly dispersed throughout the base material. The one or more dyes may be configured to absorb electromagnetic energy. The second layer may be bonded or permanently attached to the posterior surface of the first layer and may be formed of a generally clear base material. The second layer may be thick enough and configured to have a corrective prescription surfaced or polished into the posterior surface thereof without effecting the first layer. The lens blank may have an optical density equal to or less than 2.

In another embodiment, a lens is configured to provide vision correction and reduce the frequency and/or severity of photophobic responses or modulate circadian cycles. The lens includes a first layer and a second layer. The first layer has an anterior surface and a posterior surface and a generally uniform thickness therebetween. The first layer is formed of a base material and one or more energy absorptive dyes generally uniformly dispersed throughout the base material. The one or more dyes are configured to absorb electromagnetic energy and produce a generally uniform color across the first layer. The second layer is bonded or permanently attached to the posterior surface of the first layer. The second layer is formed of a generally clear base material and has a posterior surface with a corrective prescription surfaced or polished therein. The lens has an optical density equal to or less than 2.

In still yet another example embodiment, a method for forming a lens that provides a corrective prescription and reduces the frequency and/or severity of photophobic responses or modulate circadian cycles is provided. The method includes mixing one or more energy absorbing dyes into a base material to produce a generally homogeneous mixture of the base material and dye(s). The method also includes forming a first layer of a lens blank with the mixture of the base material and the dye(s), the first layer having an anterior surface and a posterior surface and providing the lens with an optical density equal to or less than 2. The method also includes forming a second layer on the posterior surface of the first layer, the second layer being formed of a base material and having a posterior surface opposite to the first layer. The method also includes surfacing or polishing the posterior surface of the second layer with a corrective prescription.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present application relates to eyewear. More specifically, the present application relates to eyewear with one or more lenses that can be polished with a user's prescription and that can reduce the frequency and/or severity of photophobic responses or modulate circadian cycles.

Figures 1, 2:
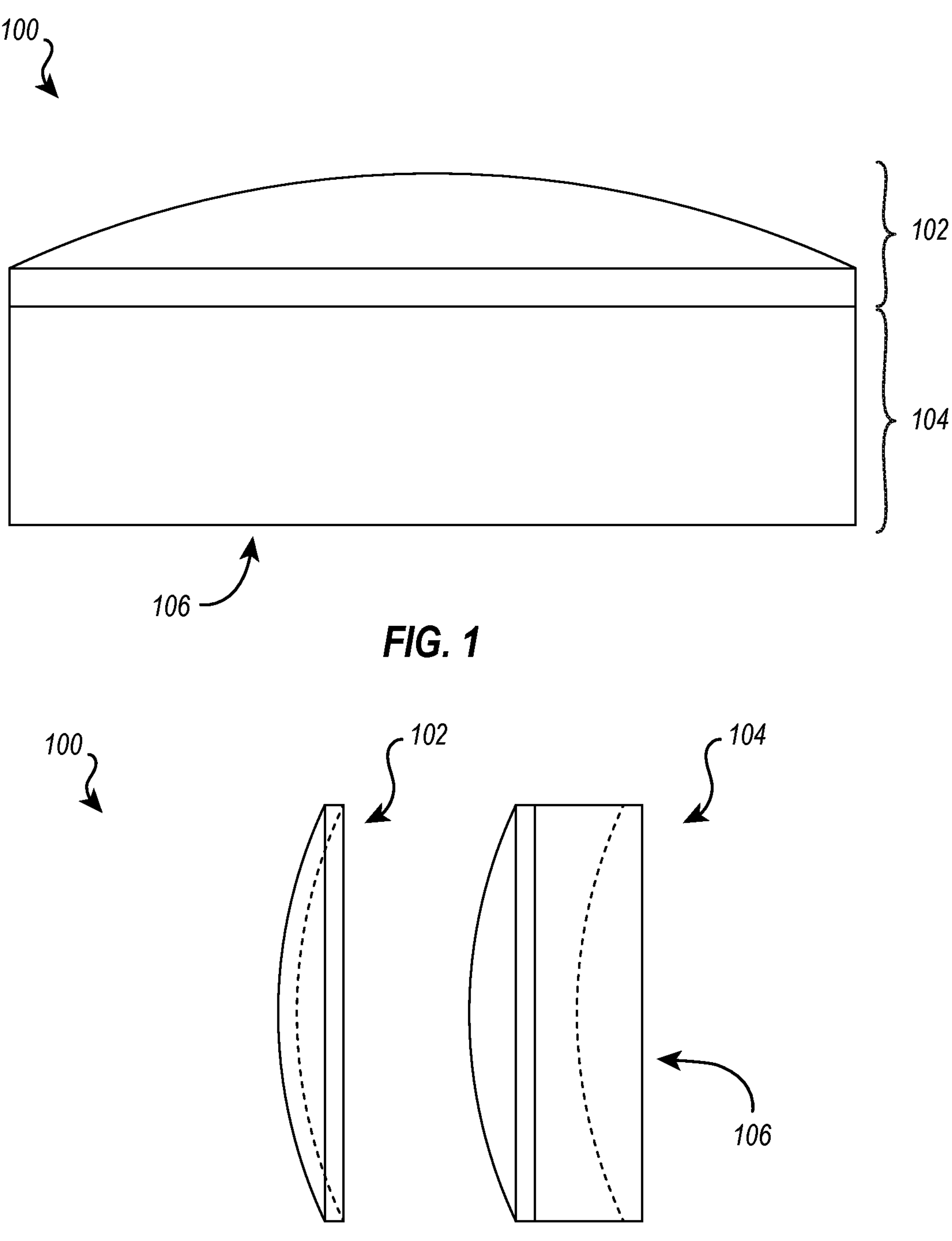
FIG. 1 illustrates a side view a lens blank according to an example embodiment of the present disclosure.
FIG. 2 illustrates an exploded view of the lens blank of FIG. 1.
Figure 3:
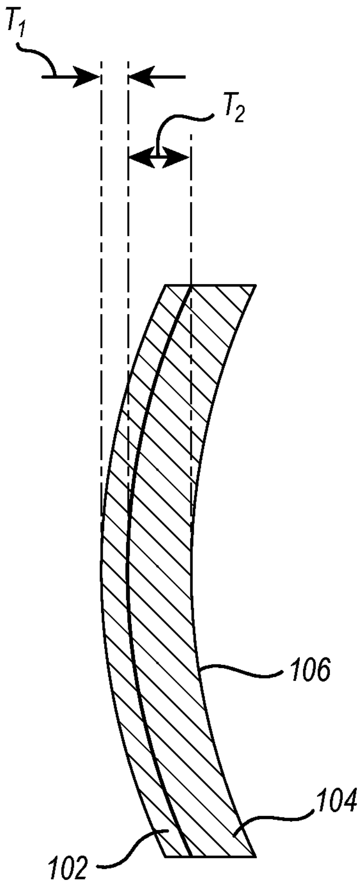
FIG. 3 illustrates a cross-sectional view of the lens blank of FIG. 1.

Attention is now directed to the Figures, which illustrate example embodiments of lenses that may provide the benefits and functionality discussed herein. For instance, FIGS. 1-3 illustrate side, exploded, and cross-sectional views of a lens blank 100 that may be used to create a prescription lens that can reduce the frequency and/or severity of photophobic responses or modulate circadian cycles. In the illustrated embodiment, the lens blank 100 includes two layers. The first layer 102 is an anterior layer (e.g., that will be positioned further from (compared to the second layer) or face away the user's eye) and the second layer 104 is a posterior layer (e.g., that will be positioned closer to (compared to the first layer) or face towards a user's eye).

The first layer 102 may provide the photophobic response control or circadian cycle modulation features to a lens formed from the lens blank 100. The first layer 102 may be formed from a base resin, thermoplastic, or polymer. The base material may have one or more electromagnetic energy absorptive dyes and/or other additives compounded thereto or mixed therein. The one or more other additives may include UV stabilizers. As will be discussed in greater detail below, the electromagnetic energy absorptive dyes and/or other additives may provide the lens blank 100 with one or more characteristics that reduce photophobic responses or modulate circadian cycles. Suitable electromagnetic energy absorptive dyes and/or other additives may be obtained from various suppliers, including Exciton, Epolin, QCR Solutions, HW Sands, Luxottica, and Moleculum. The amounts of the electromagnetic energy absorptive dyes and/or other additives added to the first layer 102 may vary depending on the amount or type of photophobic response reduction or circadian cycle modulation being sought.

The first layer 102 may have thickness T1. In some embodiments, the thickness T1 is generally uniform across the first layer 102. In some embodiments, the thickness T1 of the first layer 102 may be within a range of between about 1.5 mm to 2.0 mm. For instance, in some embodiments, the thickness T1 may be 1.6 mm. The thickness T1 may have a tolerance of +0.075 mm. The first layer 102 may also have a front radius of about 88.33 mm and a back radius of about 86.233 mm for a base curve of 6, a front radius of about 132.5 and a back radius of about 130.4 for a base curve of 4, or other values for other base curves, or values therebetween or within a reasonable variation therefrom (e.g., 1%, 5%, 10%, 25%, etc.).

As a result of the generally uniform thickness of the first layer 102, the dyes disposed within the first layer 102 may provide a generally uniform color across the first layer 102 (and across the lens blank 100). The uniform color may improve the visibility through a lens formed from the lens blank 100 compared to lenses formed from tinted glass that has a non-uniform thickness. The uniform thickness can also help ensure generally uniform optical characteristics across the first layer 102 (and thus across a lens formed from the lens blank 100).

The second layer 104 may be formed from various clear base materials (e.g., resins, thermoplastics, polymers) with different indexes of refraction. Such materials include polycarbonate, Roc Poly, urethane, nylon, and the like. In some embodiments, the base material for the second layer 104 may be the same as the base material for the first layer 102, albeit without the addition of the electromagnetic energy absorptive dyes and/or other additives. As a result, the second layer 104 may be clear.

The second layer 104 may have a thickness T2. In some embodiments, the thickness T2 is generally uniform across the second layer 104. In some embodiments, the thickness T2 of the second layer 104 may be within a range of between about 6 mm to 10 mm. For instance, in some embodiments, the thickness T2 may be about 8.4 mm. The thickness T2 may have a tolerance of +0.075 mm. This thickness T2 may be sufficient to allow the back side 106 of the second layer 104 to be polished or otherwise finished with a user's prescription, including with single vision or progressive prescriptions and with prescriptions ranging from −8 to 11+.

The second layer 104 may also have a front radius of about 88.33 mm and a back radius of about 86.233 mm for a base curve of 6, a front radius of about 132.5 and a back radius of about 130.4 for a base curve of 4, or other values for other base curves, or values therebetween or within a reasonable variation therefrom (e.g., 1%, 5%, 10%, 25%, etc.).

Figure 4:
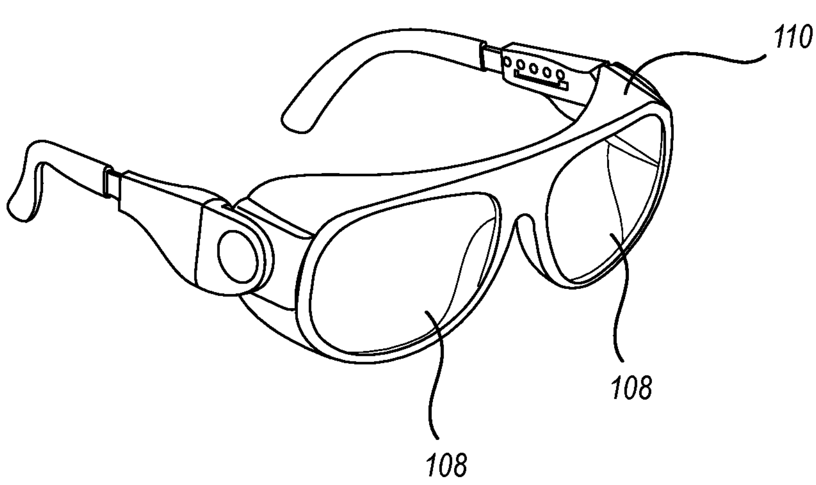
FIG. 4 illustrates an example embodiment of eyewear with lenses formed from lens blanks like those of FIGS. 1-3.

Once the lens blank 100 has been surfaced to add the user's prescription, the resulting lens 108 can be mounted within a frame 110, as shown in FIG. 4, that can be worn by a user. The resulting eyewear can thus provide the prescription polished lenses that also reduce the frequency and/or severity of photophobic responses or modulate circadian cycles.

Figure 5:
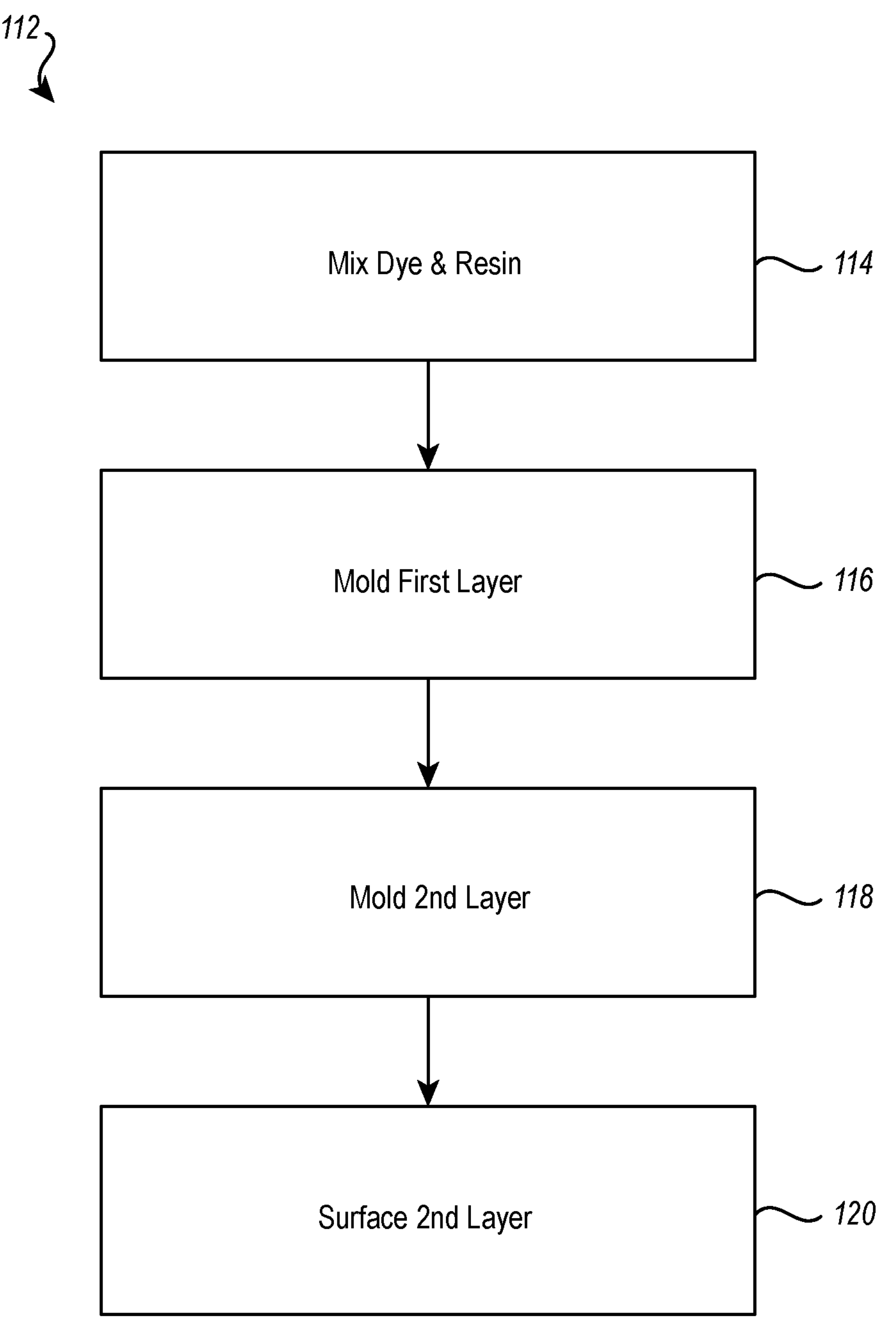
FIG. 5 illustrates an example method of making prescription lenses that reduce the frequency and/or severity of photophobic responses or modulate circadian cycles.

A method 112 for making the lens blank 100 and a lens 108 therefrom may include the steps illustrated in FIG. 5. According to the method 112, electromagnetic energy absorptive dye(s) and/or other additives are mixed with a base material (resin, thermoplastic, polymer, etc.) in a step 114. This step may include mixing the components to provide a generally uniform distribution of the dye(s) and/or other additives throughout the base material.

The method may also include a two-shot injection molding process or other process to form the lens blank 100. For instance, the method 112 may include a first (injection molding) step 116 in which the mixture of base material and dye(s) and/or other additives is disposed or injected into a mold to form the first layer 102. The method 112 may also include a second (injection molding) step 118 in which a clear base material is injected into a mold (either the same mold, or a different mold if the first layer 102 has been moved the different mold) and onto the first layer 102 to form the second layer 104. The (injection molding) process may create a strong and generally uniform bond between the first and second layers 102, 104. In some embodiments, the (two-shot injection molding) process can bond or join the first and second layers 102, 104 together such that the first and second layers 102, 104 are integrally joined into a single component. With the (two-shot injection molding) process complete, the lens blank 100 is formed.

The method 112 may also include a step 120 in which the back side 106 of the second layer 104 is surfaced or polished to form the lens 108 with a desired prescription. The resulting lens(es) 108 may then be mounted within a frame to be worn by a user.

Notably, when the back side 106 of the second layer 104 is surfaced or polished to produce the desired prescription, the first layer 102 is not surfaced or polished. Accordingly, the thickness T1 of the first layer 102 is not changed by the surfacing or polishing. As a result, the uniformity of the color across the first layer 102 remains unchanged, avoiding the color gradients common in exiting products. Likewise, the protective properties of the first layer 102 (provided by the dye(s) and/or other additives) are not altered by the surfacing or polishing of the back side 106 of the second layer 104.

As noted above, the electromagnetic energy absorptive dye(s) and/or other additives that are included in the first layer 102 may provide the lens blank 100 or lens 108 with various desired optical properties. The various optical properties, or any combinations thereof, may be selected based on the intended use of the lens 108 and may be achieved through the selection of the particular dye(s) and/or other additives and/or the amount of the dye(s) and/or other additives that are added to the first layer 102.

By way of example, particular dye(s) and/or other additives and/or their respective amounts may be added to the first layer 102 to provide the resulting lens with light filtering capabilities at one or more specific electromagnetic wavelengths or within certain electromagnetic wavelength ranges. For instance, the dye(s) and/or other additives may be selected to filter light at 470 nm, 480 nm, 484 nm, 485 nm, 490 nm, 570 nm, 580 nm, 584 nm, 587 nm, 590 nm, 600 nm, 610 nm, 620 nm, 640 nm, and/or 650 nm. Similarly, the dye(s) and/or other additives may be selected to filter light between 420 nm-540 nm, 430 nm-530 nm, 450 nm-510 nm, 460 nm-500 nm, 470 nm-490 nm, 530 nm-650 nm, 540 nm-640 nm, 560 nm-620 nm, 570 nm-610 nm, 560 nm-680 nm, 570 nm-670 nm, 580 nm-600 nm, 580 nm-640 nm, 600 nm-640 nm, and/or 610 nm-630 nm, or any ranges or values within or around the noted ranges.

In still other embodiments, the dye(s) and/or other additives may act as notch filters. The notch filters may be centered around one or more specific wavelengths and may have a specific full-width half maximum value. For instance, the dye(s) and/or other additives may act as a notch filter at 480 nm, 590 nm, and/or 620 nm with full-width half maximum values of 31 nm, 50 nm, 51 nm, 52 nm, 55 nm, 60 nm, and/or 67 nm. Likewise, particular dye(s) and/or other additives and/or their respective amounts may be added to the first layer 102 to provide the resulting lens with the desired light filtering capabilities.

Particular dye(s) and/or other additives and/or their respective amounts may be selected to provide the resulting lens with desired optical density values equal to or less than 2, 1.5, 1, or 0.5, or any value therebetween.

The combination of the thickness T1 of the first layer 102 and the particular dye(s) and/or other additives and/or their respective amounts may provide the resulting lens with desired damage threshold levels. More specifically, the thickness T1 of the first layer 102 may allow for sufficient electromagnetic energy absorptive dye(s) to be added thereto to absorb the energy from the incoming light. Further, the thickness of the first layer (and optionally the thickness of the second layer) may be sufficient to allow for the dissipation of the heat resulting from the absorption of the laser energy without resulting in damage being done to the lens. In some embodiments, the combination of the dye(s) and the thickness of the layer(s) may provide the lens with a damage threshold of about 100 watts/centimeter2. Similarly, the dye(s) and thickness of the first layer may provide the desired level of protection through a desired angle of indigence, such as from 0-30 degrees.

In accordance with the disclosure herein, one example embodiment of a lens blank may include a first layer having an anterior surface and a posterior surface and being formed a base material and one or more energy absorptive dyes generally uniformly dispersed throughout the base material. The one or more dyes may be configured to absorb electromagnetic energy. The lens blank may also include a second layer bonded or permanently attached to the posterior surface of the first layer. The second layer may be formed of a generally clear base material and have a posterior surface opposite to the first layer. The posterior surface of the second layer may be configured to be surfaced or polished with a corrective prescription without effecting the first layer. The lens blank may have an optical density equal to or less than 2.

In some embodiments, the one or more energy absorbing dyes produce a generally uniform color across the first layer.

In some embodiments, the first layer further comprises one or more UV stabilizers generally uniformly dispersed throughout the base material of the first layer.

In some embodiments, the base material of the second layer is the same type of material as the base material of the first layer.

In some embodiments, the base materials comprise a resin, thermoplastic, or polymer.

In some embodiments, the first layer has a generally uniform thickness.

In some embodiments, the thickness of the first layer is between about 1.5 mm and about 2.0 mm.

In some embodiments, the one or more energy absorptive dyes are configured to filter light at or around 480 nm, 590 nm, and/or 620 nm.

In some embodiments, the second layer has a generally uniform thickness.

In some embodiments, the thickness of the second layer is between about 6 mm and 10 nm.

In some embodiments, the second layer has a thickness sufficient to have a full progressive prescription surfaced or polished into the posterior surface thereof without effecting the first layer.

In another example embodiment, a lens is configured to provide vision correction and laser protection. The lens may include a first layer having an anterior surface and a posterior surface and a generally uniform thickness therebetween. The first layer may be formed of a base material and one or more energy absorptive dyes generally uniformly dispersed throughout the base material. The one or more dyes may be configured to absorb electromagnetic energy and may produce a generally uniform color across the first layer. The lens may also include a second layer bonded or permanently attached to the posterior surface of the first layer. The second layer may be formed of a generally clear base material and having a posterior surface with a corrective prescription surfaced or polished therein. The lens may have an optical density equal to or less than 2.

In some embodiments, the thickness of the first layer is between about 1.5 mm and about 2.0 mm.

In some embodiments, the corrective prescription is a full progressive prescription.

In some embodiments, the second layer has a non-polished or non-surfaced thickness of between about 6 mm and about 10 mm.

In some embodiments, the one or more energy absorptive dyes are configured to filter light at or around 480 nm, 590 nm, and/or 620 nm.

In another example embodiment, a method for forming a prescription and laser protective lens is provided. The method includes mixing one or more energy absorbing dyes into a base material to produce a generally homogeneous mixture of the base material and dye(s). The method also includes forming a first layer of a lens blank with the mixture of the base material and the dye(s), the first layer having an anterior surface and a posterior surface and providing the lens with an optical density equal to or less than 2. The method also includes forming a second layer on the posterior surface of the first layer, the second layer being formed of a base material, the second layer having a posterior surface opposite to the first layer. The method may also include surfacing or polishing the posterior surface of the second layer with a corrective prescription.

In some embodiments, forming the first layer comprises inserting the mixture of the base material and dye(s) into a mold.

In some embodiments, forming the second layer comprises inserting the base material of the second layer into the mold and on the posterior surface of the first layer.

In some embodiments, the method also includes selecting the one or more dyes and amounts thereof to filter light at or around 480 nm, 590 nm, and/or 620 nm.

The terms "approximately," "about," "near," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A lens blank, comprising:

a first layer having an anterior surface and a posterior surface and being formed of a polymeric base material and one or more electromagnetic energy absorptive dyes homogeneously dispersed throughout the bulk of the base material, the first layer having a generally uniform thickness, the thickness of and/or a dye dispersion in the first layer being sufficient to maintain a generally uniform optical density equal to or less than 2 and a generally uniform color after surfacing or polishing of a corrective prescription; and a second layer formed of a clear polymeric material co-molded with and integrally bonded to the posterior surface of the first layer so as to form a single, unitary lens blank, the second layer having a posterior surface opposite to the first layer, the posterior surface of the second layer being configured to be surfaced or polished with a corrective prescription without removal or alteration of the first layer, the second layer having a thickness sufficient to receive the corrective prescription such that surfacing or polishing removes material only from the second layer and does not reduce the thickness, change the optical density, or alter the generally uniform color of the first layer, the lens blank having an optical density equal to or less than 2.

2. The lens blank of claim 1, wherein the one or more energy absorbing dyes produce a generally uniform color across the first layer.

3. The lens blank of claim 1, wherein the first layer further comprises one or more UV stabilizers generally uniformly dispersed throughout the base material of the first layer.

4. The lens blank of claim 1, wherein the base material of the second layer is the same type of material as the base material of the first layer.

5. The lens blank of claim 4, wherein the base materials comprise a resin, thermoplastic, or polymer.

6. The lens blank of claim 1, wherein the generally uniform thickness of the first layer is such that the one or more electromagnetic energy absorptive dyes provide a generally uniform color across the first layer and avoid color gradients after surfacing or polishing of the corrective prescription.

7. The lens blank of claim 1, wherein the thickness of the first layer is between about 1.5 mm and about 2.0 mm.

8. The lens blank of claim 1, wherein the second layer has a generally uniform unsurfaced or unpolished thickness.

9. The lens blank of claim 8, wherein the thickness of the second layer is between about 6 mm and 10 mm.

10. The lens blank of claim 1, wherein the second layer has a thickness sufficient to have a full progressive prescription surfaced or polished into the posterior surface thereof without effecting the first layer.

11. A lens configured to provide vision correction and attenuation of electromagnetic energy, the lens comprising:

a first layer having an anterior surface and a posterior surface and a generally uniform thickness therebetween, the first layer being formed of a polymeric base material and one or more electromagnetic energy absorptive dyes homogeneously dispersed throughout the bulk of the base material, the one or more dyes being configured to absorb electromagnetic energy, one or more energy absorbing dyes producing a generally uniform color across the first layer the thickness of and/or a dye dispersion of the first layer being sufficient to maintain a generally uniform optical density equal to or less than 2 and the generally uniform color after surfacing or polishing of a corrective prescription; and a second layer formed of a generally clear polymeric material co-molded with and integrally bonded to the posterior surface of the first layer to form a single, unitary body, the second layer having a posterior surface with a corrective prescription surfaced or polished therein, the second layer having a thickness sufficient to contain the corrective prescription such that surfacing or polishing removes material only from the second layer without reducing a thickness or altering optical properties of the first layer, wherein the first layer remains unaltered during the surfacing or polishing of the corrective prescription, such that the generally uniform thickness and color of the first layer are preserved across the lens, and the lens has an optical density equal to or less than 2.

12. The lens of claim 11, wherein the thickness of the first layer is between about 1.5 mm and about 2.0 mm.

13. The lens of claim 11, wherein the corrective prescription is a full progressive prescription.

14. The lens of claim 11, wherein the second layer has a non-polished or non-surfaced thickness of between about 6 mm and about 10 mm.

15. A method for forming a prescription and laser protective lens, the method comprising:

mixing one or more electromagnetic energy absorbing dyes into a polymeric base material to produce a generally homogeneous mixture of the base material and dye(s);

molding the homogeneous mixture to form a first layer of a lens blank, the first layer having an anterior surface and a posterior surface, the dyes being homogeneously dispersed throughout the bulk of the first layer to provide the lens with an optical density equal to or less than 2, the first layer being formed with a generally uniform thickness and with the thickness and/or a dye distribution sufficient to maintain a generally uniform optical density equal to or less than 2 and a generally uniform color after subsequent surfacing or polishing;

co-molding a generally clear polymeric material directly onto the posterior surface of the first layer to form a second layer integrally bonded to the first layer so as to create a single, unitary lens blank, the second layer having a posterior surface opposite to the first layer, the second layer being formed with a thickness sufficient to receive a corrective prescription; and surfacing or polishing the posterior surface of the second layer with a corrective prescription without removing or altering any portion of the first layer, wherein surfacing or polishing removes material only from the second layer and does not reduce the thickness, change the optical density, or alter a generally uniform color of the first layer.

16. The method of claim 15, wherein molding the first layer comprises injecting the mixture of the base material and dye(s) into a mold.

17. The method of claim 16, wherein co-molding the second layer comprises inserting the base material of the second layer into the same mold while the first layer remains therein so that the layers become integrally bonded.

* * * * *